(12) United States Patent
Maruyama

(10) Patent No.: US 9,120,726 B2
(45) Date of Patent: Sep. 1, 2015

(54) RADIATION-SENSITIVE RESIN COMPOSITION, COMPOUND AND PRODUCING METHOD OF COMPOUND

(75) Inventor: Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 13/525,563

(22) Filed: Jun. 18, 2012

(65) Prior Publication Data

US 2012/0258399 A1    Oct. 11, 2012

Related U.S. Application Data

(63) Continuation of application No. PCT/JP2010/071890, filed on Dec. 7, 2010.

(30) Foreign Application Priority Data

Dec. 25, 2009   (JP) .................................. 2009-294433

(51) Int. Cl.
| | | |
|---|---|---|
| *G03F 7/004* | (2006.01) | |
| *C07C 309/75* | (2006.01) | |
| *G03F 7/039* | (2006.01) | |

(52) U.S. Cl.
CPC ............ *C07C 309/75* (2013.01); *G03F 7/0045* (2013.01); *C07C 2102/10* (2013.01); *C07C 2102/20* (2013.01); *C07C 2102/22* (2013.01); *C07C 2103/18* (2013.01); *G03F 7/0392* (2013.01)

(58) Field of Classification Search
None
See application file for complete search history.

(56) References Cited

U.S. PATENT DOCUMENTS

| | | | |
|---|---|---|---|
| 3,748,132 A | 7/1973 | Arcesi et al. | |
| 4,143,023 A * | 3/1979 | Mark et al. .................... | 524/156 |
| 2004/0031408 A1 | 2/2004 | Makino | |

FOREIGN PATENT DOCUMENTS

| | | | |
|---|---|---|---|
| JP | 54-016562 | | 2/1979 |
| JP | 06202335 A | * | 7/1994 |
| JP | 2000-035665 | | 2/2000 |
| JP | 2004-216716 | | 8/2004 |

(Continued)

OTHER PUBLICATIONS

Machine translation JP 06-202335. Jul. 22, 1994.*

(Continued)

*Primary Examiner* — Cynthia H Kelly
*Assistant Examiner* — Alyssa L Cepluch
(74) *Attorney, Agent, or Firm* — Oblon, McClelland, Maier & Neustadt, L.L.P.

(57) ABSTRACT

A radiation-sensitive resin composition includes a compound shown by a following general formula (A), a solvent and a resin having an acid-labile group. Each of $R^1$ and $R^2$ independently represents a substituted or unsubstituted monovalent hydrocarbon group having 1 to 25 carbon atoms. Each of X and Z independently represents a substituted or unsubstituted divalent hydrocarbon group having 1 to 25 carbon atoms. Y represents a single bond or the like. n represents an integer from 0 to 5.

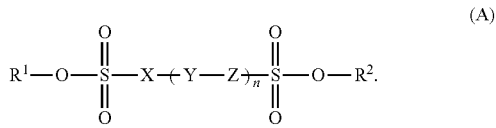

11 Claims, 1 Drawing Sheet

(56) References Cited

FOREIGN PATENT DOCUMENTS

| | | | |
|---|---|---|---|
| JP | 2005-025150 | | 1/2005 |
| JP | 2005025150 A | * | 1/2005 |
| JP | 2005-088346 | | 4/2005 |
| JP | 2007052182 A | * | 3/2007 |
| JP | 2008-096743 | | 4/2008 |

OTHER PUBLICATIONS

Machine translation JP 2005-025150. Jan. 27, 2005.*
Machine translation JP 2007-052182. Mar. 1, 2007.*
International Search Report for corresponding International Application No. PCT/JP2010/071890, Mar. 15, 2011.
Written Opinion for corresponding International Application No. PCT/JP2010/071890, Mar. 15, 2011.

* cited by examiner

RADIATION-SENSITIVE RESIN COMPOSITION, COMPOUND AND PRODUCING METHOD OF COMPOUND

CROSS-REFERENCE TO RELATED APPLICATIONS

The present application is a continuation application of International Application No. PCT/JP2010/071890, filed Dec. 7, 2010, which claims priority to Japanese Patent Application No. 2009-294433, filed Dec. 25, 2009. The contents of these applications are incorporated herein by reference in their entirety.

BACKGROUND OF THE INVENTION

1. Field of the Invention

The invention relates to a radiation-sensitive resin composition, a compound and a producing method of a compound.

2. Discussion of the Background

Until now, lithographic microfabrication using a photoresist composition has been performed in a semiconductor device (e.g., IC or LSI) production process. Recently, along with an increase in the degree of integration of integrated circuits, it has been required to form a sub-micrometer or quarter-micrometer ultrafine pattern.

In order to deal with such a requirement, it has been studied to utilize the shorter exposure wavelength. More specifically, though g-lines were used previously, i-lines, KrF excimer laser light, ArF excimer laser light, and the like have been used in recent years. And currently, development of lithography that utilizes electron beams, X-rays, or EUV light other than above excimer laser light has been advanced. Above all, lithography that utilizes EUV light is expected to be next-generation or third-generation patterning technology, and development of a positive type resist that exhibits high sensitivity and high resolution has been desired.

In a positive type resist, high sensitivity is very important task in order to achieve to reduce the wafer processing time. However, if high sensitivity is pursued in a positive type resist that utilizes EUV light, nano edge roughness may deteriorate in addition to decrease the resolution. Therefore, development of a resist that satisfies all of these characteristics has been desired.

Incidentally, the term "nano edge roughness" may also be referred to as "line edge roughness (LER)", and shows the height of asperity (roughness) generated on the side face of a line part of a resist pattern. Since such an asperity (roughness) are transferred during an etching (transfer) step that utilizes the resist as a mask, the electrical properties of an integrated circuit may deteriorate. In particular, in the case of lithography that utilizes EUV light, since it may cause the electrical properties of an integrated circuit to deteriorate even if asperity (roughness) is fine, it is very important task to improve the nano edge roughness.

In order to solve these problems, particularly in order to achieve a task of high sensitivity, it is disclosed that an acid proliferation agent that self-catalytically generates the other acid by using an acid generated from a radiation-sensitive acid-generating agent as catalyst is added to a radiation-sensitive resin composition (see JP-A-2000-35665 and JP-A-2008-96743, for example).

SUMMARY OF THE INVENTION

According to one aspect of the present invention, a radiation-sensitive resin composition includes a compound shown by a following general formula (A), a solvent and a resin having an acid-labile group.

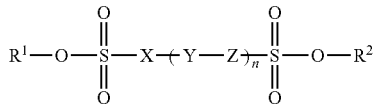

Each of $R^1$ and $R^2$ independently represents a substituted or unsubstituted monovalent hydrocarbon group having 1 to 25 carbon atoms. Each of X and Z independently represents a substituted or unsubstituted divalent hydrocarbon group having 1 to 25 carbon atoms. Y represents a single bond or any one of groups shown by following formulas (1-1) to (1-6). n represents an integer from 0 to 5.

According to another aspect of the present invention, a compound is shown by a following general formula (A).

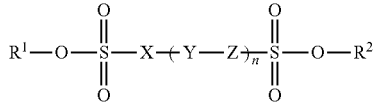

Each of $R^1$ and $R^2$ independently represents a substituted or unsubstituted monovalent hydrocarbon group having 1 to 25 carbon atoms. Each of X and Z independently represents a substituted or unsubstituted divalent hydrocarbon group having 1 to 25 carbon atoms. Y represents a single bond or any one of groups shown by following formulas (1-1) to (1-6). n represent s an integer from 0 to 5.

-continued

(1-5)

(1-6)

According to further aspect of the present invention, a producing method of a compound includes reacting a compound shown by a general formula (a1), a compound shown by a general formula (a2), and a compound shown by a general formula (a3).

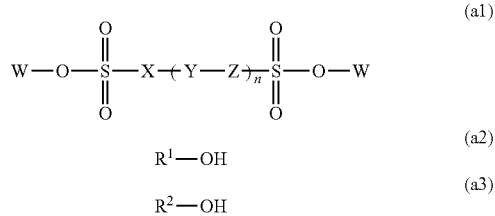

(a1)

(a2)

(a3)

Each of X and Z independently represents a substituted or unsubstituted divalent hydrocarbon group having 1 to 25 carbon atoms. Y represents a single bond or any one of groups shown by formulas (1-1) to (1-6).

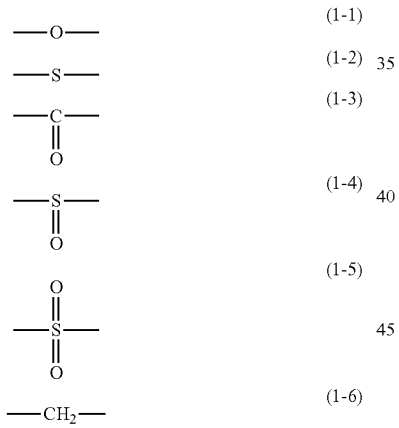

(1-1)
(1-2)
(1-3)
(1-4)
(1-5)
(1-6)

Each W independently represents a halogen atom. n represents an integer from 0 to 5. Each of $R^1$ in the general formula (a2) and $R^2$ in the general formula (a3) independently represents a substituted or unsubstituted monovalent hydrocarbon group having 1 to 25 carbon atoms.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DESCRIPTION OF THE EMBODIMENTS

Figure 1:
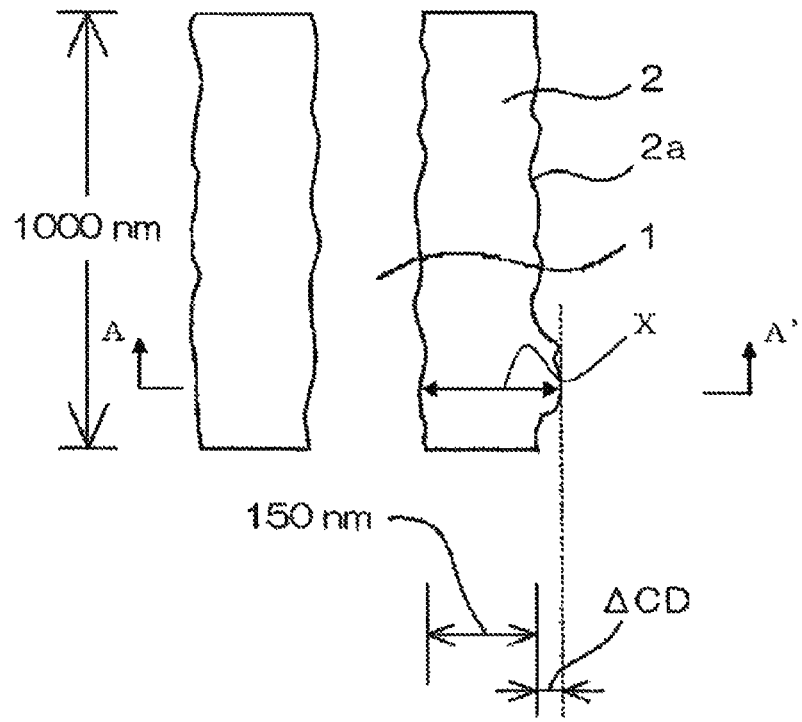
FIG. 1 is a plan view schematically showing a line-and-space pattern.

According to embodiments of the present invention, the following radiation-sensitive resin composition, compound (A) included therein, and producing method of the compound are provided.

[1] A radiation-sensitive resin composition including a compound (A) shown by following general formula (A), a solvent (B), and a resin (C) having an acid-labile group,

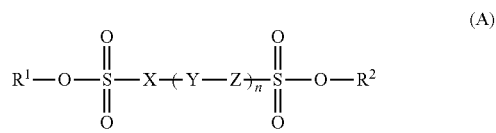

(A)

wherein $R^1$ and $R^2$ independently represent a substituted or unsubstituted monovalent hydrocarbon group having 1 to 25 carbon atoms, X and Z independently represent a substituted or unsubstituted divalent hydrocarbon group having 1 to 25 carbon atoms, Y represents a single bond or any one of groups shown by following formulas (1-1) to (1-6), and n represents an integer from 0 to 5,

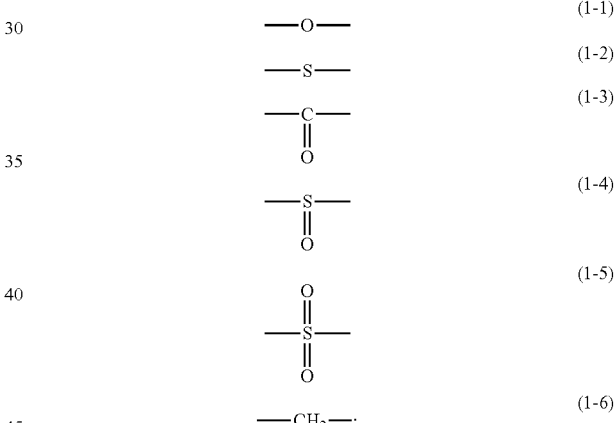

(1-1)
(1-2)
(1-3)
(1-4)
(1-5)
(1-6)

[2] The radiation-sensitive resin composition according to [1], wherein the compound (A) is at least one compound selected from a group consisting of compounds shown by following general formulas (A1) to (A5),

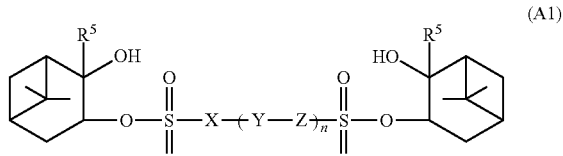

(A1)

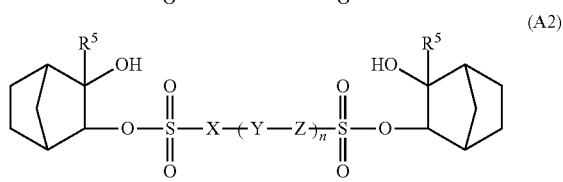

(A2)

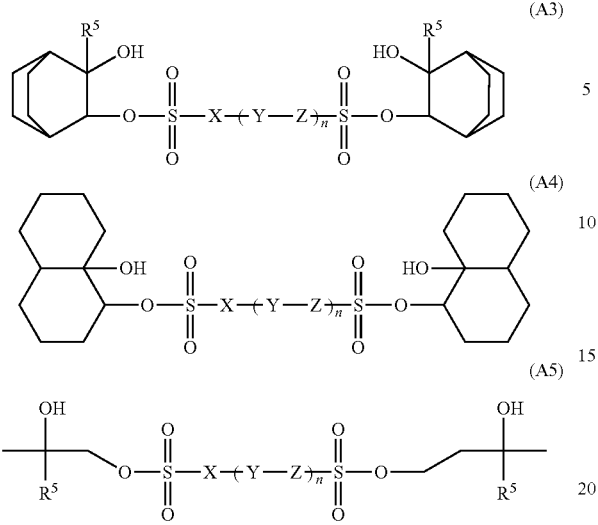

(A3)

(A4)

(A5)

wherein X and Z independently represent a substituted or unsubstituted divalent hydrocarbon group having 1 to 25 carbon atoms, Y represents a single bond or any one of groups shown by the formulas (1-1) to (1-6), n represents an integer from 0 to 5, and $R^5$ independently represent a substituted or unsubstituted hydrocarbon group having 1 to 25 carbon atoms.

[3] The radiation-sensitive resin composition according to [2], wherein X and Z in the general formulas (A1) to (A5) independently represent a substituted or unsubstituted divalent aromatic group having 1 to 25 carbon atoms.

[4] The radiation-sensitive resin composition according to [2] or [3], wherein Y in the general formulas (A1) to (A5) represents a single bond, the group shown by the formula (1-1), or the group shown by the formula (1-6).

[5] The radiation-sensitive resin composition according to any one of [1] to [4], wherein $R^1$ and $R^2$ in the general formula (A) independently represent a substituted or unsubstituted monovalent hydrocarbon group having 1 to 25 carbon atoms and a tertiary hydroxyl group.

[6] A compound shown by following general formula (A),

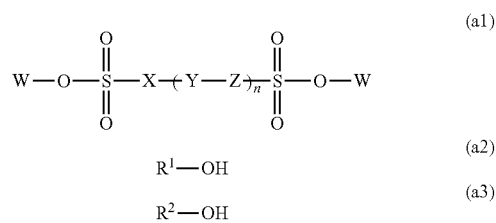

(A)

wherein $R^1$ and $R^2$ independently represent a substituted or unsubstituted monovalent hydrocarbon group having 1 to 25 carbon atoms, X and Z independently represent a substituted or unsubstituted divalent hydrocarbon group having 1 to 25 carbon atoms, Y represents a single bond or any one of groups shown by following formulas (1-1) to (1-6), and n represents an integer from 0 to 5,

—O—  (1-1)

—S—  (1-2)

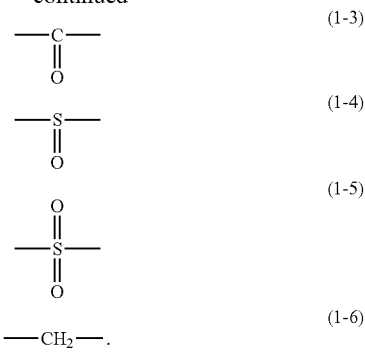

[7] The compound according to [6], wherein $R^1$ and $R^2$ in the general formula (A) independently represent a substituted or unsubstituted monovalent hydrocarbon group having 1 to 25 carbon atoms and a tertiary hydroxyl group.

[8] A producing method of a compound including reacting a compound (a1) shown by following general formula (a1), a compound (a2) shown by following general formula (a2), and a compound (a3) shown by following general formula (a3),

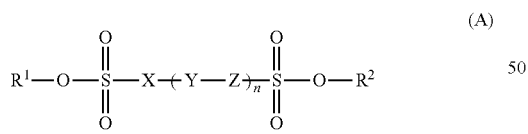

(a1)

$R^1$—OH  (a2)

$R^2$—OH  (a3)

wherein X and Z independently represent a substituted or unsubstituted divalent hydrocarbon group having 1 to 25 carbon atoms, Y represents a single bond or any one of groups shown by following formulas (1-1) to (1-6), W independently represent a halogen atom, n represents an integer from 0 to 5, and $R^1$ in the general formula (a2) and $R^2$ in the general formula (a3) independently represent a substituted or unsubstituted monovalent hydrocarbon group having 1 to 25 carbon atoms,

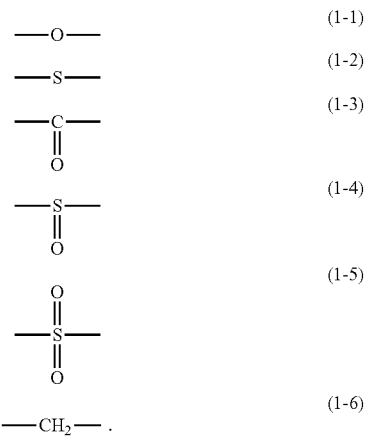

[9] The producing method of a compound according to [8], wherein $R^1$ in the general formula (a2) and $R^2$ in the general formula (a3) independently represent a substituted or unsubstituted monovalent hydrocarbon group having 1 to 25 carbon atoms and a tertiary hydroxyl group.

The radiation-sensitive resin composition according to the embodiment of the present invention can form a resist film that exhibits high sensitivity and excellent resolution, and can form a resist pattern that is superior in nano edge roughness.

The compound according to the embodiment of the present invention constitutes a radiation-sensitive resin composition capable of forming a resist film that exhibits high sensitivity and excellent resolution, and capable of forming a resist pattern that is superior in nano edge roughness.

The producing method of a compound according to the embodiment of the present invention can produce an acid proliferation agent included in a radiation-sensitive resin composition capable of forming a resist film that exhibits high sensitivity and excellent resolution, and capable of forming a resist pattern that is superior in nano edge roughness.

The embodiments will now be described with reference to the accompanying drawings, wherein like reference numerals designate corresponding or identical elements throughout the various drawings. However, the present invention is not limited to the following exemplary embodiments. It should be understood that the one which made various modifications and improvements to the following exemplary embodiments without departing from the scope of the invention based on the knowledge of a person having ordinary skill in the art are also included in the scope of the present invention.

1. Radiation-Sensitive Resin Composition

A radiation-sensitive resin composition according to the embodiment of the present invention includes a compound (A), a solvent (B), and a resin (C) having an acid-labile group (hereinafter may be referred to as "resin (C)"). Moreover, the radiation-sensitive resin composition according to the embodiment of the present invention normally further includes a radiation-sensitive acid-generating agent (hereinafter may be referred to as "acid-generating agent (D)").

The radiation-sensitive resin composition having the above constituent can form a resist film that exhibits high sensitivity and excellent resolution, and can form a resist pattern that is superior in nano edge roughness. That is, the radiation-sensitive resin composition according to the embodiment of the present invention can form a chemically-amplified positive type resist film that effectively is sensitive to (extreme) far-ultraviolet rays such as KrF excimer laser, ArF excimer laser, EUV, X-rays such as synchrotron radiation, or electron beams, exhibits excellent sensitivity, and can stably and accurately form a fine pattern. In addition, there is an advantage that a resist that exhibits good sensitivity may make the wafer processing time shorten.

1-1. Compound (A)

The compound (A) according to the embodiment of the present invention is an acid proliferation agent (hereinafter may be referred to as "acid proliferation agent (A)"). The acid proliferation agent is a compound that is decomposed due to an acid to generate the other acid. Therefore, once an acid has been generated from the radiation-sensitive acid-generating agent upon application of radiation, the acid proliferation agent (A) generates the other acid due to the acid generated from the radiation-sensitive acid-generating agent, and then reacts self-catalytically, so that a large amount of acid can be generated. That is, the radiation-sensitive resin composition including the acid proliferation agent (A) improves the solubility of the exposed area of the resist in an alkaline developer, and makes the apparent sensitivity as the resist improve. Incidentally, the acid proliferation agent (A) is stable as long as an acid does not exist together. The compound (A) may be used in almost the same content ratio as that of a known acid proliferation agent used for a conventional radiation-sensitive resin composition.

The acid proliferation agent (A) is a compound shown by the following general formula (A).

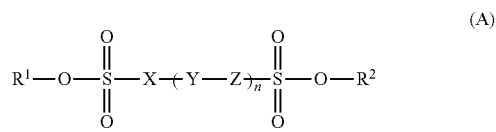

(A)

wherein $R^1$ and $R^2$ independently represent a substituted or unsubstituted monovalent hydrocarbon group having 1 to 25 carbon atoms, X and Z independently represent a substituted or unsubstituted divalent hydrocarbon group having 1 to 25 carbon atoms, Y represents a single bond or any one of groups shown by the following formulas (1-1) to (1-6), and n represents an integer from 0 to 5. Incidentally, n is preferably 1 or 2 from the viewpoint that the nano edge roughness becomes better.

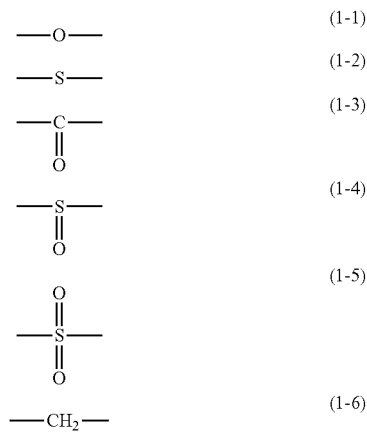

Examples of the unsubstituted monovalent hydrocarbon group having 1 to 25 carbon atoms represented by $R^1$ and $R^2$ in the general formula (A) include a chain-like hydrocarbon group, a cyclic hydrocarbon group, and the like.

Examples of the chain-like hydrocarbon group include a linear alkyl group having 1 to 10 carbon atoms.

Examples of the cyclic hydrocarbon group include a monocyclic or polycyclic aliphatic hydrocarbon group having 1 to 25 carbon atoms. Specific examples of the cyclic hydrocarbon group include a polycyclic aliphatic hydrocarbon group having 6 to 10 carbon atoms. More specific examples of the cyclic hydrocarbon group include the groups shown by the following formulas (x-1) to (x-5).

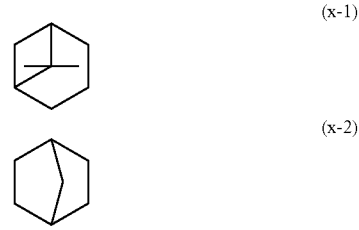

(x-3)

(x-4)

(x-5)

Examples of a substituent among the substituted monovalent hydrocarbon group having 1 to 25 carbon atoms represented by $R^1$ and $R^2$ in the general formula (A) include an alkyl group, an alkoxy group, an alkoxycarbonyl group, a hydroxyl group, a cyano group. That is, specific examples of the substituted monovalent hydrocarbon group having 1 to 25 carbon atoms include a group obtained by substituting at least one hydrogen atom of the unsubstituted monovalent hydrocarbon group having 1 to 25 carbon atoms with such a substituent.

In particular, in the case that the hydrocarbon group represented by $R^1$ and $R^2$ includes a hydroxyl group (i.e., in the case that the hydrocarbon group represented by $R^1$ and $R^2$ includes a hydroxyl group as a substituent), it is preferable that the storage stability of the acid proliferation agent (A) becomes good.

It is preferable that $R^1$ and $R^2$ in the general formula (A) independently represent a substituted or unsubstituted monovalent hydrocarbon group having 1 to 25 carbon atoms and a tertiary hydroxyl group. In such a case, a resist that exhibits good sensitivity and excellent thermal stability can be obtained.

Examples of the substituted or unsubstituted divalent hydrocarbon group having 1 to 25 carbon atoms represented by X and Z in the general formula (A) include a substituted or unsubstituted divalent aliphatic group having 1 to 25 carbon atoms, a substituted or unsubstituted divalent aromatic group having 1 to 25 carbon atoms, a substituted or unsubstituted divalent heterocyclic group having 1 to 25 carbon atoms.

Examples of the aliphatic group include a chain-like or cyclic (including bridged carbocyclic) alkylene group. The number of carbon atoms of these aliphatic groups is preferably 1 to 12, and more preferably 1 to 8.

Specific examples of the aliphatic group include a methylene group, an ethylene group, a propylene group, a butylene group, a pentene group, a hexene group, a cyclohexyl group, a cyclooctyl group, a bicyclic hydrocarbon group, and a tricyclic hydrocarbon group.

Examples of the aromatic group include an aryl group or an arylalkyl group. Incidentally, the aromatic group may be either a monocyclic structure or a polycyclic structure.

Specific examples of the aromatic group include a phenyl group, a tolyl group, a benzyl group, a phenethyl group, a naphthyl group, and a naphthylmethyl group.

At least one hydrogen atom of the aliphatic group or the aromatic group may be substituted with a substituent. That is, the aliphatic group or the aromatic group may be substituted aliphatic group or substituted aromatic group. Examples of a substituent that substitute hydrogen atom include a fluorine atom, a linear or branched alkyl group having 1 to 12 carbon atoms such as a trifluoromethyl group, a nonafluorobutyl group, a methyl group, an ethyl group, an n-propyl group, an i-propyl group, an n-butyl group, a 2-methylpropyl group, a 1-methylpropyl group, a t-butyl group, and the like; a linear or branched alkoxy group having 1 to 12 carbon atoms such as a methoxy group, an ethoxy group, an n-propoxy group, an i-propoxy group, an n-butoxy group, a 2-methylpropoxy group, a 1-methylpropoxy group, a t-butoxy group, and the like.

Examples of the heterocyclic group include a group derived from a known various heterocyclic compounds. Incidentally, the heterocyclic group may be either a monocyclic structure or a polycyclic structure.

Specific examples of the heterocyclic group include a 5-membered cyclic compound having one heteroatom such as furan, pyrrole, benzofuran, indole, carbazole, and the like, and a fused ring compound thereof; a 5-membered cyclic compound having two heteroatoms such as oxazole, pyrazole and the like, and a fused ring compound thereof; a 6-membered cyclic compound having one heteroatom such as pyran, pyrone, coumarin, pyridine, quinoline, isoquinoline, acridine, and the like, and a fused ring compound thereof; a 6-membered cyclic compound having two heteroatoms such as pyridazine, pyrimidine, pyrazine, phthalazine, and the like, and a fused ring compound thereof.

From the viewpoint of forming the resist that exhibits good sensitivity and excellent thermal stability, it is preferable that the acid proliferation agent (A) is at least one compound selected from the group consisting of compounds (A1) to (A5) shown by the following general formulas (A1) to (A5), more preferable that X and Z in the general formulas (A1) to (A5) independently represent a substituted or unsubstituted divalent aromatic group having 1 to 25 carbon atoms. In particular, it is preferable that the acid proliferation agent (A) is a compound in which both ends (i.e., groups that correspond to $R^1$ and $R^2$ in the general formula (A)) include a tertiary hydroxyl group and has an identical structure. Moreover, it is preferable that Y in the general formulas (A1) to (A5) represents a single bond, the group shown by the formula (1-1), or the group shown by the formula (1-6). In this case, a resist that exhibits better sensitivity and more excellent thermal stability can be obtained.

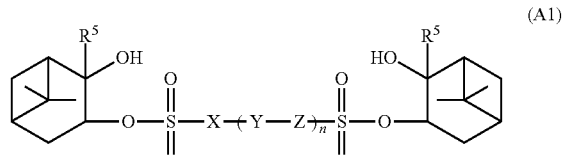
(A1)

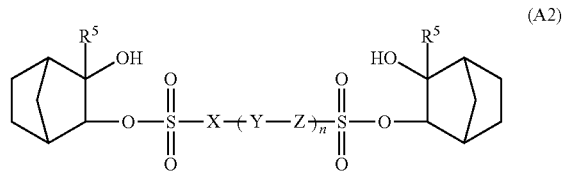
(A2)

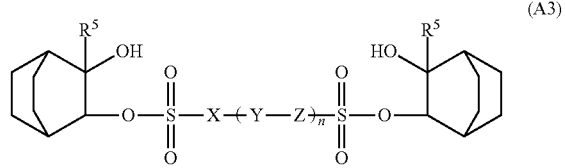
(A3)

-continued

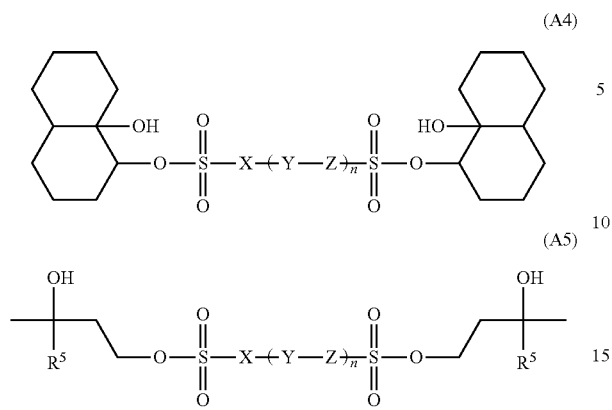

(A4)

(A5)

R⁵ in the general formulas (A1) to (A5) independently represent a substituted or unsubstituted hydrocarbon group having 1 to 25 carbon atoms. Note that X, Y, Z, and n in the general formulas (A1) to (A5) are the same as defined for X, Y, Z, and n in the general formula (A). R⁵ represents a substituent that substitutes the (substituted) hydrocarbon group having 1 to 25 carbon atoms represented by R¹ and R².

Specific examples of the acid proliferation agent (A) include the compounds shown by the following formulas (A1-1) to (A1-10), (A2-1), (A3-1), (A4-1), and (A5-1).

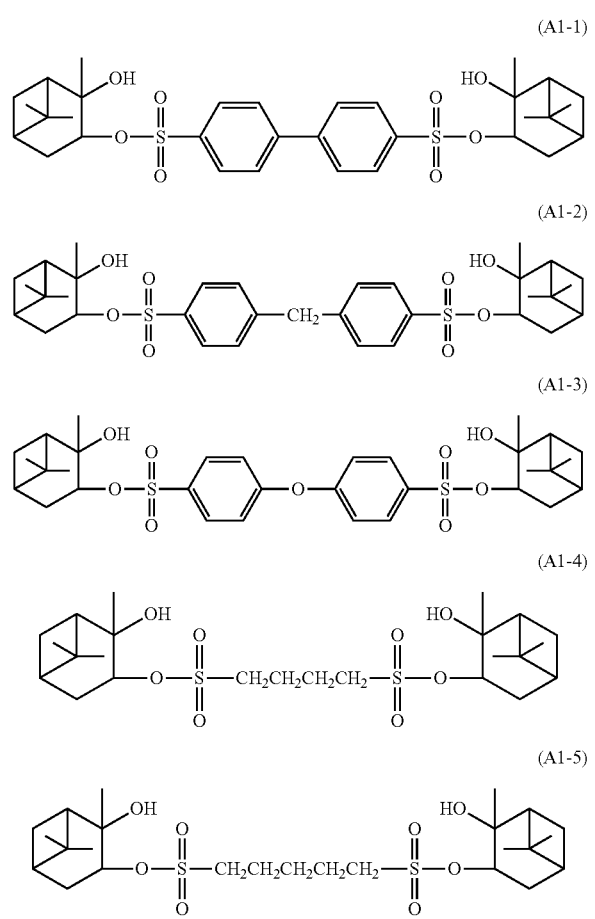

(A1-1)

(A1-2)

(A1-3)

(A1-4)

(A1-5)

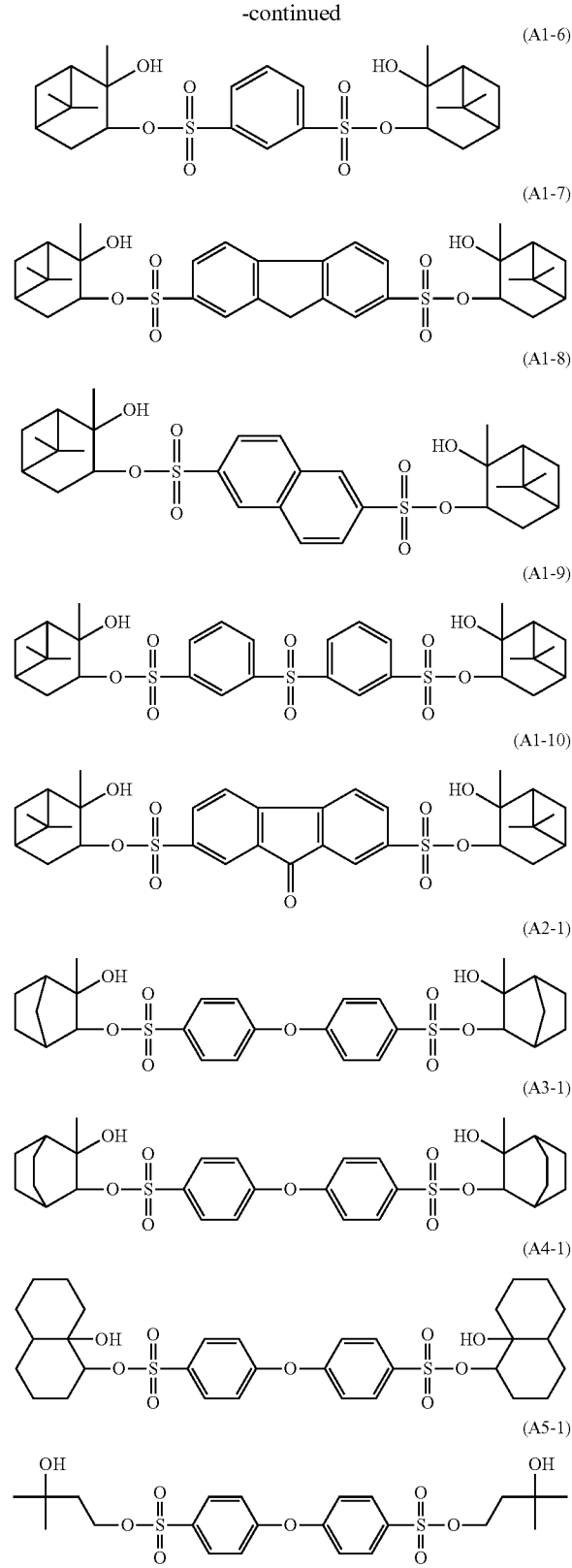

(A1-6)

(A1-7)

(A1-8)

(A1-9)

(A1-10)

(A2-1)

(A3-1)

(A4-1)

(A5-1)

Among these, from the viewpoint that the resist that exhibits further high sensitivity is obtained, the compounds shown by the formulas (A1-1), (A1-2), (A1-3), (A2-1), (A3-1), and (A5-1) are preferable.

1-1-1. Producing Method of Acid Proliferation Agent (A)

A producing method of the compound (acid proliferation agent (A)) according to the embodiment of the present invention includes reacting a compound (a1) shown by the following general formula (a1), a compound (a2) shown by the following general formula (a2), and a compound (a3) shown by the following general formula (a3). More specifically, the compound (acid proliferation agent (A)) according to the embodiment of the present invention may be synthesized by reacting the sulfonic halide (a1) shown by the following general formula (a1), the compound (a2) shown by the following general formula (a2), and the compound (a3) shown by the following general formula (a3) in dichloromethane in the presence of a base.

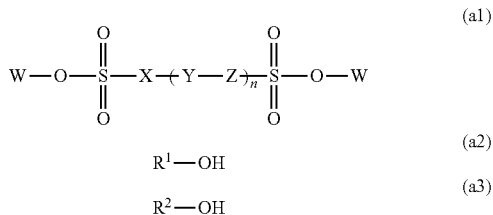

$$R^1-OH \quad (a2)$$
$$R^2-OH \quad (a3)$$

wherein X and Z independently represent a substituted or unsubstituted divalent hydrocarbon group having 1 to 25 carbon atoms, Y represents a single bond or any one of the groups shown by the following formulas (1-1) to (1-6), W independently represent a halogen atom, n represents an integer from 0 to 5, and $R^1$ in the general formula (a2) and $R^2$ in the general formula (a3) independently represent a substituted or unsubstituted monovalent hydrocarbon group having 1 to 25 carbon atoms.

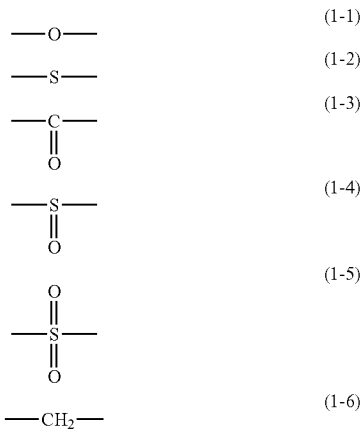

Note that X, Y, Z, and n in the general formula (a1) are the same as defined for X, Y, Z, and n in the general formula (A), and $R^1$ in the general formula (a2) and $R^2$ in the general formula (a3) are the same as defined for $R^1$ and $R^2$ the general formula (A).

Cl is particularly preferable as the halogen atom represented by W in the general formula (a1). Moreover, it is preferable that X and Z in the general formula (a1) independently represent a substituted or unsubstituted divalent aromatic group having 1 to 25 carbon atoms. And, it is preferable that Y represents a single bond, the group shown by the formula (1-1), or the group shown by the formula (I-6). In the case that X, Y, and Z satisfy the above conditions, the acid proliferation agent (A) capable of obtaining a resist that exhibits further good sensitivity and excellent thermal stability is obtained.

It is preferable that $R^1$ in the general formula (a2) and $R^2$ in the general formula (a3) independently represent a substituted or unsubstituted monovalent hydrocarbon group having 1 to 25 carbon atoms and a tertiary hydroxyl group. In this case, the acid proliferation agent (A) capable of obtaining a resist that exhibits good sensitivity and excellent thermal stability is synthesized.

It is preferable that one hydrogen atom of the group represented by $R^1$ in the general formula (a2) and the group represented by $R^2$ in the general formula (a3) are substituted with a hydroxyl group. That is, it is preferable that the compounds (a2) and (a3) are a diol.

In the case that the compounds (a2) and (a3) are a diol, it is particularly preferable that one of the two hydroxyl groups is a tertiary hydroxyl group.

Moreover, it is also preferable that the group represented by $R^1$ in the general formula (a2) and the group represented by $R^2$ in the general formula (a3) have an identical structure (i.e., $R^1=R^2$).

In the case that the acid proliferation agent (A) is a compound obtained by the above producing method, a resist that exhibits good sensitivity and excellent thermal stability can be obtained.

As to compounds (a2) and (a3), in the case of synthesizing the compounds (A1) to (A4), since hydroxyl groups are respectively bonded to two adjacent carbon atoms in the ring structure, there exists geometric isomers having cis configuration and trans configuration. In the embodiment of the present invention, either geometric isomer having cis configuration or geometric isomer having trans configuration may be used. Note that it is preferable to use the geometric isomer having cis configuration from the viewpoint of thermal stability.

The reaction conditions such as reaction temperature or reaction time are not particularly limited. Known reaction conditions may be employed.

The solvent is not particularly limited during reaction. Note that it is preferably dichloromethane, acetonitrile, tetrahydrofuran (THF), or the like. These solvents may be used either alone or in combination.

The base is not particularly limited during reaction. Note that it is preferably to use 4-dimethylaminopyridine, 1,4-diazabicyclo[2,2,2]octane, triethylamine, or the like. These bases may be used either alone or in combination.

1-2. Solvent (B)

As the solvent (B), a known one may be used without particularly limited. Of all others, at least one selected from the group consisting of linear, branched, or cyclic ketones, propylene glycol monoalkyl ether acetates, alkyl 2-hydroxypropionates, alkyl 3-alkoxypropionates, γ-butyrolactone, and the like is preferable.

The content ratio of solvent (B) is preferably the amount that the total solid content of the radiation-sensitive resin composition is 1 to 20 mass %, more preferably 1 to 15 mass %, and particularly preferably 1 to 10 mass %. If the content ratio of solvent (B) is less than 1 mass %, it may be difficult to apply the radiation-sensitive resin composition due to high viscosity. On the other hand, if the content ratio of solvent (B) is exceeds 20 mass %, it may be difficult to form a resist film having a sufficient thickness.

1-3. Resin (C)

The resin having acid-labile group (resin (C)) is a resin which includes a repeating unit having acid-labile group, and is insoluble or scarcely soluble in an alkali. The acid-labile group is deprotected (dissociates) due to an acid generated by the acid-generating agent (D) upon application of radiation, so that the resin (C) becomes readily soluble in an alkali.

Note that the expression "insoluble or scarcely soluble in an alkali" used in this specification means such a property that 50% (50 nm) or more of the initial thickness remain when a film of 100 nm in the thickness having been formed by using only the resin (C) is subjected instead of a resist film formed by the radiation-sensitive resin composition including resin (C) to develop under alkaline development conditions, which employed for forming a resist pattern using a resin film formed of the radiation-sensitive resin composition.

By including such a resin (C), the radiation-sensitive resin composition according to the embodiment of the present invention can form a chemically-amplified positive type resist film that effectively is sensitive to electron beams or extreme ultraviolet rays during a lithographic process, and can stably and accurately form a fine pattern. The resin (C) may be used in almost the same content ratio as that of a known resin having an acid-labile group used for a conventional radiation-sensitive resin composition.

1-3-1. Component of Resin (C)

As the repeating unit having an acid-labile group included in the resin (C), the repeating unit which makes the acid-labile group dissociate due to an acid may be used without particularly limited. Note that it is preferable that the repeating unit is at least one of the following repeating units (c1) and (c2). There is an advantage that a resist pattern that exhibits good sensitivity can be formed by utilizing at least one of the repeating units (c1) and (c2) as the repeating unit having an acid-labile group.

(1) Repeating Unit (c1)

The repeating unit (c1) is the repeating unit shown by the following general formula (c1).

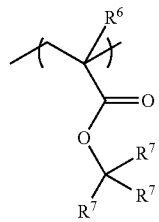

(c1)

wherein $R^6$ represents a hydrogen atom, a methyl group, a trifluoromethyl group, or a hydroxymethyl group, and $R^7$ independently represent a monovalent alicyclic hydrocarbon group having 4 to 20 carbon atoms, or a linear or branched alkyl group having 1 to 4 carbon atoms, or any two of $R^7$ bond to each other to form a divalent alicyclic hydrocarbon group together with the carbon atom bonded thereto, and the remaining $R^7$ represents a monovalent alicyclic hydrocarbon group having 4 to 20 carbon atoms, or a linear or branched alkyl group having 1 to 4 carbon atoms.

Specific examples of the monovalent alicyclic hydrocarbon group having 4 to 20 carbon atoms represented by $R^7$ in the general formula (c1) include a group having an alicyclic ring derived from a cycloalkanes such as norbornane, tricyclodecane, tetracyclododecane, adamantane, cyclobutane, cyclopentane, cyclohexane, cycloheptane, or cyclooctane; a group obtained by substituting at least one hydrogen atom of the group having an alicyclic ring with at least one substituent selected from the group consisting of linear, branched, or cyclic alkyl groups having 1 to 4 carbon atoms, such as a methyl group, an ethyl group, an n-propyl group, an i-propyl group, an n-butyl group, a 2-methylpropyl group, a 1-methylpropyl group, and a t-butyl group.

Specific examples of the linear or branched alkyl group having 1 to 4 carbon atoms represented by $R^7$ in the general formula (c1) include a methyl group, an ethyl group, an n-propyl group, an i-propyl group, an n-butyl group, a 2-methylpropyl group, a 1-methylpropyl group, a t-butyl group.

Examples of the divalent alicyclic hydrocarbon group formed by being bonded any two of $R^7$ to each other along with the carbon atom bonded thereto in the general formula (c1) include a group having an alicyclic ring derived from norbornane, tricyclodecane, tetracyclododecane, adamantane, cyclopentane, or cyclohexane; a group obtained by substituting at least one hydrogen atom of the group having an alicyclic ring with an alkyl group having 1 to 4 carbon atoms.

The repeating unit (c1) is preferably any of repeating units shown by the following general formulas (c1-1) to (c1-7).

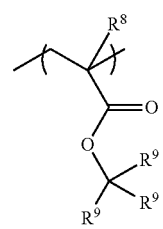

(c1-1)

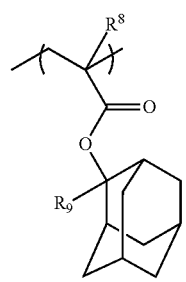

(c1-2)

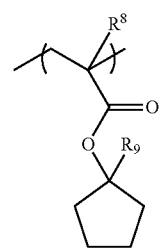

(c1-3)

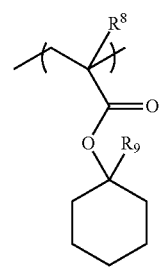

(c1-4)

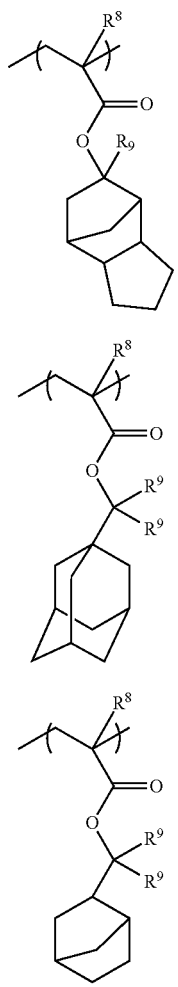

(c1-5)

(c1-6)

(c1-7)

wherein $R^8$ represents a hydrogen atom, a methyl group, a trifluoromethyl group, or a hydroxymethyl group, and $R^9$ represents or independently represent a linear or branched alkyl group having 1 to 4 carbon atoms.

Among these, the repeating units shown by the general formulas (c1-2), (c1-3), or (c1-4) are preferable as the repeating unit (c1). When the resin (C) includes above repeating unit, there is an advantage that the radiation-sensitive resin composition according to the embodiment of the present invention can form a resist pattern that is superior in nano edge roughness.

(2) Repeating Unit (c2)

The repeating unit (c2) is the repeating unit shown by the following general formula (c2).

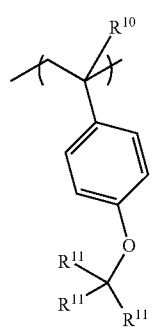

(c2)

wherein $R^{10}$ represents a hydrogen atom, a methyl group, a trifluoromethyl group, or a hydroxymethyl group, and $R^{11}$ independently represent a monovalent alicyclic hydrocarbon group having 4 to 20 carbon atoms, or a linear or branched alkyl group having 1 to 4 carbon atoms, or any two of $R^{11}$ bond to each other to form a divalent alicyclic hydrocarbon group together with the carbon atom bonded thereto, and the remaining $R^{11}$ represents a monovalent alicyclic hydrocarbon group having 4 to 20 carbon atoms, or a linear or branched alkyl group having 1 to 4 carbon atoms.

Examples of the group represented by $R^{11}$ in the general formula (c2) include those mentioned above in connection with the groups shown by $R^7$ in the general formula (c1). Note that $R^{11}$ preferably independently represent a linear or branched alkyl group having 1 to 4 carbon atoms.

The resin (C) may include only one type of these repeating units having acid-labile group, or may include two or more types of these repeating units having acid-labile group.

It is preferable that the resin (C) further include at least one repeating unit selected from the group consisting of the following repeating units (c3) to (c5) other than these repeating units having acid-labile group. When the resin (C) includes at least one repeating unit selected from the group consisting of the repeating units (c3) to (c5), there is an advantage that the radiation-sensitive resin composition according to the embodiment of the present invention can form a resist film that forms a resist pattern being superior in nano edge roughness.

(3) Repeating Unit (c3)

The repeating unit (c3) is the repeating unit shown by the following general formula (c3).

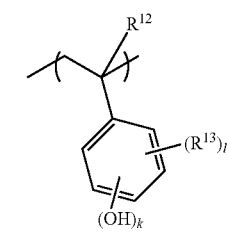

(c3)

wherein $R^{12}$ represents a hydrogen atom or a methyl group, $R^{13}$ represents a linear or branched alkyl group having 1 to 12 carbon atoms, or a linear or branched alkoxy group having 1 to 12 carbon atoms, k represents an integer from 0 to 3, and l represents an integer from 0 to 3, provided that k+l satisfies the relation of $0 \leq k+l \leq 5$, and a plurality of $R^{13}$ may be either identical or different in the case that l is 2 or 3.

Specific examples of the linear or branched alkyl group having 1 to 12 carbon atoms shown by $R^{13}$ in the general formula (c3) include a methyl group, an ethyl group, an n-propyl group, an i-propyl group, an n-butyl group, a 2-methylpropyl group, a 1-methylpropyl group, a t-butyl group. Among these, a methyl group, an ethyl group, an n-butyl group, and a t-butyl group are preferable from the viewpoint of forming a resist pattern that is superior in nano edge roughness.

Specific examples of the linear or branched alkoxy group having 1 to 12 carbon atoms shown by $R^{13}$ in the general formula (c3) include a methoxy group, an ethoxy group, an n-propoxy group, an i-propoxy group, an n-butoxy group, a 2-methylpropoxy group, a 1-methylpropoxy group, a t-butoxy group. Among these, a methoxy group and an ethoxy group are preferable from the viewpoint of forming a resist pattern that is superior in nano edge roughness.

In the general formula (c3), k is preferably 1 or 2, and l is preferably an integer from 0 to 2.

(4) Repeating Unit (c4)

The repeating unit (c4) is the repeating unit shown by the following general formula (c4).

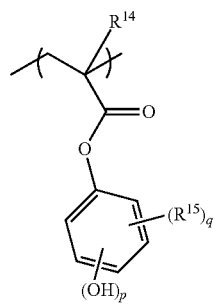

wherein $R^{14}$ represents a hydrogen atom or a methyl group, $R^{15}$ represents a linear or branched alkyl group having 1 to 12 carbon atoms, or a linear or branched alkoxy group having 1 to 12 carbon atoms, p represents an integer from 1 to 3, and q represents an integer from 0 to 3, provided that p+q satisfies the relation of 0≤p+q≤5, and a plurality of $R^{15}$ may be either identical or different in the case that q is 2 or 3.

Specific examples of the group shown by $R^{15}$ in the general formula (c4) include those mentioned above in connection with the groups shown by $R^{13}$ in the general formula (c3).

In the general formula (c4), p is preferably 1 or 2, and q is preferably 0 or 1.

(5) Repeating Unit (c5)

The repeating unit (c5) is the repeating unit shown by the following general formula (c5).

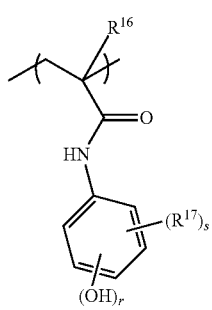

wherein $R^{16}$ represents a hydrogen atom or a methyl group, $R^{17}$ represents a linear or branched alkyl group having 1 to 12 carbon atoms, or a linear or branched alkoxy group having 1 to 12 carbon atoms, r represents an integer from 1 to 3, and s represents an integer from 0 to 3, provided that r+s satisfies the relation of 0≤r+s≤5, and a plurality of $R^{17}$ may be either identical or different in the case that s is 2 or 3.

Specific examples of the group shown by $R^{17}$ in the general formula (c5) include those mentioned above in connection with the groups shown by $R^{13}$ in the general formula (c3).

In the general formula (c5), r is preferably 1 or 2 and s is preferably 0 or 1.

The resin (C) may further include a repeating unit derived from a non-acid-labile compound (hereinafter referred to as "repeating unit (c6)") other than the repeating units (c1) to (c5). When the resin (C) includes the repeating unit (c6), there is an advantage that the radiation-sensitive resin composition according to the embodiment of the present invention can form a resist film that forms a resist pattern being superior in nano edge roughness.

(6) Repeating Unit (c6)

The term "non-acid-labile compound" is a compound that does not include a group (acid-labile group) that dissociates due to an acid. Specific examples of the non-acid-labile compound that produces the repeating unit (c6) include styrene, α-methylstyrene, 4-methylstyrene, 2-methylstyrene, 3-methylstyrene, isobornyl acrylate, tricyclodecanyl (meth)acrylate, tetracyclododecenyl(meth)acrylate, the compound shown by the following formula (c6-1), the compound shown by the following formula (c6-2). Among these, styrene, α-methylstyrene, 4-methylstyrene, 2-methylstyrene, 3-methylstyrene, tricyclodecanyl acrylate, the compound shown by the formula (c6-1), or the compound shown by the following formula (c6-2) are preferable. The resin (C) may include only one type of repeating unit (c6), or may include two or more types of repeating unit (c6). Note that the term "(meth)acrylate" in this specification means "acrylate" or "methacrylate".

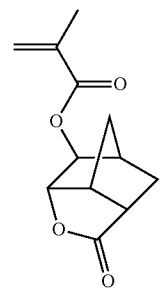

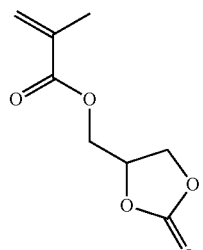

The content ratio of the repeating unit (c1) in the resin (C) is preferably 1 mol % or more, more preferably 20 to 70 mol %, and particularly preferably 20 to 60 mol %, based on all of the repeating units (=100 mol %) included in the resin (C). If the content ratio of the repeating unit (c1) is less than 1 mol %, nano edge roughness of the resulting resist pattern may deteriorate. Incidentally, if the content ratio of the repeating unit (c1) is 20 mol % or more, a resist pattern being superior in nano edge roughness can be formed.

The content ratio of the repeating unit (c2) in the resin (C) is preferably 1 mol % or more, more preferably 20 to 70 mol %, and particularly preferably 20 to 60 mol %, based on all of the repeating units (=100 mol %) included in the resin (C). If the content ratio of the repeating unit (c2) is less than 1 mol %, nano edge roughness of the resulting resist pattern may deteriorate. If the content ratio of the repeating unit (c2) is 20 mol % or more, a resist pattern being superior in nano edge roughness can be formed.

The total content ratio of the repeating units (c3) to (c5) in the resin (C) is preferably 1 mol % or more, more preferably 10 to 95 mol %, and particularly preferably 40 to 80 mol %, based on all of the repeating units (=100 mol %) included in the resin (C). If the total content ratio of the repeating units (c3) to (c5) is less than 1 mol % or exceeds 95 mol %, nano edge roughness of the resulting resist pattern may deteriorate.

The total content ratio of the repeating units (c1) to (c5) in the resin (C) is preferably 10 mol % or more, more preferably 40 to 100 mol %, and particularly preferably 50 to 100 mol %, based on all of the repeating units (=100 mol %) included in the resin (C). If the total content ratio of the repeating units (c1) to (c5) is less than 10 mol %, nano edge roughness of the resulting resist pattern may deteriorate. Incidentally, if the total content ratio of the repeating units (c1) to (c5) is 10 mol % or more, a resist pattern being superior in nano edge roughness can be formed.

The content ratio of the repeating unit (c6) in the resin (C) is preferably 60 mol % or less, and more preferably 0 to 50 mol %, based on all of the repeating units (=100 mol %) included in the resin (C). If the content ratio of the repeating unit (c6) exceeds 60 mol %, nano edge roughness of the resulting resist pattern may deteriorate. Incidentally, if the content ratio of the repeating unit (c6) is 60 mol % or less, a resist pattern that keeps a good balance between resolution and nano edge roughness can be formed.

1-3-2. Producing Method of Resin (C)

Producing method of resin (C) is not particularly limited. For example, the resin (C) may be synthesized by an arbitrary method such as radical polymerization, anionic polymerization, or the like. The hydroxystyrene unit constituting the side-chain in the repeating units (c3) to (c5) may be obtained by hydrolyzing, for example, the acetoxy group in the obtained resin (C) in an organic solvent in the presence of a base or an acid.

The polystyrene-reduced weight average molecular weight (hereinafter referred to as "Mw") of the resin (C) determined by gel permeation chromatography (GPC) is preferably 3,000 to 100,000, more preferably 3,000 to 40,000, and particularly preferably 3,000 to 25,000.

The ratio (Mw/Mn) of the Mw to the polystyrene-reduced number average molecular weight (hereinafter referred to as "Mn") of the resin (C) determined by GPC is preferably 1 to 5, more preferably 1 to 3, and particularly preferably 1 to 2.5.

1-4. Radiation-Sensitive Acid-Generating Agent (D)

The acid-generating agent (D) generates an acid due to radiation applied to the resist during a lithographic process. The acid-labile group included in the resin (C) is deprotected (dissociates) due to an acid generated by the acid-generating agent (D) and the other acid generated by the acid proliferation agent (A).

The acid-generating agent (D) is preferably at least one compound selected from the group consisting of onium salts, diazomethane compounds, and sulfonimide compounds from the viewpoint that the acid generation efficiency, heat resistance, and the like is good. Incidentally, these acid-generating agents (D) may be used either alone or in combination.

The content ratio of the acid-generating agent (D) is preferably 0.1 to 40 parts by mass, and more preferably 0.5 to 30 parts by mass, based on 100 parts by mass of the resin (C). If the content ratio of the acid-generating agent (D) is less than 0.1 parts by mass, the sensitivity and the developability may deteriorate. On the other hand, if the content ratio of the acid-generating agent (D) exceeds 40 parts by mass, the transparency to radiation, the pattern shape, the heat resistance, and the like may deteriorate.

1-5. Acid Diffusion Controller (E)

The radiation-sensitive resin composition according to the embodiment of the present invention preferably further includes an acid diffusion controller (E). The acid diffusion controller (E) controls a phenomenon in which an acid generated from the acid-generating agent (D) upon exposure is diffused in the resist film to inhibit undesired chemical reactions in the unexposed area.

The storage stability of the resulting radiation-sensitive resin composition is improved by adding the acid diffusion controller (E) to the radiation-sensitive resin composition. Moreover, the acid diffusion controller (E) further improves the resolution of the resulting resist film, and minimizes a change in line width of the resist pattern due to a variation in post-exposure delay (PED) from exposure to post-exposure bake, so that a radiation-sensitive resin composition that is remarkably superior process stability can be obtained.

Examples of the acid diffusion controller (E) include a nitrogen-containing organic compound and a photosensitive basic compound.

(1) Nitrogen-Containing Organic Compound

Examples of the nitrogen-containing organic compounds include a compound shown by the following general formula (E1), a compound having two nitrogen atoms in the molecule, a polyamino compound or a polymer having three or more nitrogen atoms, an amide group-containing compound, a urea compound, a nitrogen-containing heterocyclic compound.

(E1)

wherein $R^{26}$ independently represent a hydrogen atom, a substituted or unsubstituted linear, branched, or cyclic alkyl group, a substituted or unsubstituted aryl group, or a substituted or unsubstituted aralkyl group.

(2) Photosensitive Basic Compound

The photosensitive basic compound is a photosensitive component that is efficiently decomposed into neutral fragments in the exposed area, and remains as it is without decomposed in the unexposed area. Since such a photosensitive basic compound can effectively utilize an acid generated in the exposed part (i.e. exposed area), and it is possible to improve sensitivity as compared with a non-photosensitive basic compound.

The photosensitive basic compound is not particularly limited as long as the photosensitive basic compound has the above properties. Note that examples of the photosensitive basic compound include compounds shown by the following general formulas (E2-1) and (E2-2).

(E2-1)

(E2-2)

wherein $R^{27}$ independently represent a substituted or unsubstituted linear or branched alkyl group having 1 to 10 carbon atoms or a substituted or unsubstituted aryl group having 6 to 18 carbon atoms, or any two of $R^{27}$ bond to each other to form a cyclic structure together with the sulfur atom, and the remaining $R^{27}$ represents a substituted or unsubstituted linear or branched alkyl group having 1 to 10 carbon atoms or a substituted or unsubstituted aryl group having 6 to 18 carbon atoms, and $R^{28}$ independently represent a substituted or unsubstituted linear or branched alkyl group having 1 to 10 carbon atoms or a substituted or unsubstituted aryl group having 6 to 18 carbon atoms, or two of $R^{28}$ bond to each other to form a cyclic structure together with the iodine atom.

$U^-$ in the general formulas (E2-1) and (E2-2) represents $OH^-$, $R^-$, or $R-COO^-$, and R represents a monovalent organic group.

$U^-$ preferably represents $OH^-$, $CH_3COO^-$, or any of the anions shown by the following formulas (e2-1) to (e2-5).

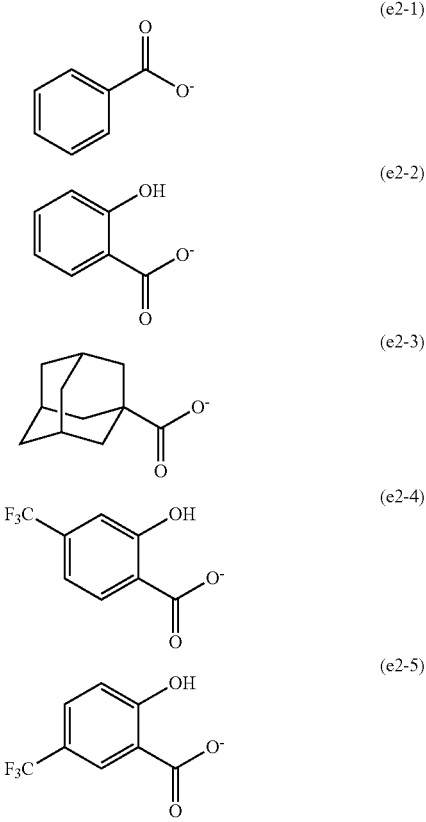

The photosensitive basic compound is preferably a triphenylsulfonium compound wherein the anion moiety ($U^-$) is $OH^-$, $CH_3COO^-$, or any of the anions shown by the formulas (e2-2), (e2-3), and (e2-4).

Incidentally, these acid diffusion controllers (E) may be used either alone or in combination.

The content ratio of the acid diffusion controller (E) is preferably 30 parts by mass or less, more preferably 0.001 to 30 parts by mass, and particularly preferably 0.005 to 20 parts by mass, based on 100 parts by mass of the resin (C). If the content ratio of the acid diffusion controller (E) exceeds 30 parts by mass, the sensitivity of the resulting resist film, or the developability of the exposed area may deteriorate. Incidentally, if the content ratio of the acid diffusion controller (E) is less than 0.001 parts by mass, the pattern shape or the dimensional accuracy of the resulting resist film may deteriorate depending on the process conditions.

1-6. Additive (F)

The radiation-sensitive resin composition according to the embodiment of the present invention may optionally include an additive such as surfactant, sensitizer, aliphatic additive, dye, pigment, adhesion improver, halation inhibitor, preservative, and anti-foaming agent, and the like other than the acid proliferation agent (A), the solvent (B), the resin (C), the acid-generating agent (D), and the acid diffusion controller (E).

(1) Surfactant

The surfactant is the component that improves the applicability, striation, developability, and the like of the resist.

Incidentally, these surfactants may be used either alone or in combination.

The content ratio of the surfactant is preferably 0.001 to 2 parts by mass based on 100 parts by mass of the resin (C).

(2) Sensitizer

The sensitizer is the component that absorbs the energy of radiation, and transmits the energy to the acid-generating agent (D) to increase the amount of acid, and has an effect that the apparent sensitivity of the radiation-sensitive resin composition is improved.

Examples of the sensitizer include carbazoles, acetophenones, benzophenones, naphthalenes, phenols, biacetyl, eosine, rose bengal, pyrenes, anthracenes, phenothiazines.

Incidentally, these sensitizers may be used either alone or in combination.

The content ratio of the sensitizer is preferably 0.1 to 10 parts by mass based on 100 parts by mass of the resin (C).

(3) Aliphatic Additive

The aliphatic additive is the component that further improves the dry etching resistance, the pattern shape, the adhesion to a substrate, and the like.

Specific examples of the aliphatic additive include adamantane derivatives such as 1-adamantanecarboxylic acid, 2-adamantanon, t-butyl 1-adamantanecarboxylate, t-butoxycarbonylmethyl 1-adamantanecarboxylate, α-butyrolactone 1-adamantanecarboxylate, di-t-butyl 1,3-adamantanedicarboxylate, t-butyl 1-adamantaneacetate, t-butoxycarbonylmethyl 1-adamantaneacetate, di-t-butyl 1,3-adamantanediacetate, and 2,5-dimethyl-2,5-di(adamantylcarbonyloxy)hexane;

deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; alkylcarboxylates such as dimethyl adipate, diethyl adipate, dipropyl adipate, di-n-butyl adipate, and di-t-butyl adipate; 3-[2-hydroxy-2,2-bis(trifluoromethyl)ethyl]tetracyclo[$4.4.0.1^{2,5}.1^{7,10}$]dodecane.

Incidentally, these aliphatic additives may be used either alone or in combination.

The content ratio of the aliphatic additive is preferably 0.5 to 20 parts by mass based on 100 parts by mass of the resin (C). If the content ratio of the aliphatic additive exceeds 20 parts by mass, heat resistance of the resulting resist film may be reduced.

The dye or pigment visualizes the latent image in the exposed area to mitigate the effects of halation during exposure.

The adhesion improver improves the adhesion of the resulting resist film to a substrate.

1-7. Usage of Radiation-Sensitive Resin Composition

The radiation-sensitive resin composition according to the embodiment of the present invention may be useful as a material capable of forming a chemically-amplified positive type resist film, and may form a positive type resist pattern having a desired shape.

In the case of forming a resist pattern using the radiation-sensitive resin composition according to the embodiment of the present invention, the radiation-sensitive resin composition is applied to a substrate to form a resist film at first. The radiation-sensitive resin composition may have been filtered through a filter having a pore size of about 0.2 μm after adjusting the total solid content, for example. A silicon wafer, an aluminum-coated wafer, or the like may be used as the substrate. The radiation-sensitive resin composition may be applied by an arbitrary method. More specifically, the radiation-sensitive resin composition may be applied by spin coating, cast coating, roll coating, or the like.

After that, the resist film may optionally be pre-baked (hereinafter referred to as "PB") at about 70 to 160° C.

The resist film is then exposed so that a desired resist pattern is formed. Examples of radiation that may be used for exposure include (extreme) far-ultraviolet rays such as KrF excimer laser (wavelength: 248 nm), ArF excimer laser (wavelength: 193 nm), EUV (extreme ultraviolet rays, wavelength: 13.5 nm), X-rays such as synchrotron radiation, charged particle rays such as electron beams (EB). The exposure conditions such as dose may be appropriately selected depending on the composition of the radiation-sensitive resin composition, the type of additive, and the like. Note that liquid immersion lithography may also be used as the exposure process.

It is preferable that the post-exposure bake (hereinafter referred to as "PEB") is subjected after exposure. It is possible to dissociate the acid-labile group included in the resin (C) more smoothly by subjecting the PEB. The heat condition of PEB may be appropriately selected depending on the composition of the radiation-sensitive resin composition. Note that heat condition of PEB is preferably at 30 to 200° C., and more preferably at 50 to 170° C.

In the embodiment of the present invention, in order to maximize the potential of the radiation-sensitive resin composition, an organic or inorganic antireflective film may be formed on the substrate as is disclosed in, for example JP-A-H6-12452 (JP-A-S59-93448). Moreover, in order to inhibit the effect of basic impurities or the like exists under the environmental atmosphere, a protective film may be formed on the resist film so that the resist film is not affected by basic impurities and the like contained in the environmental atmosphere as is disclosed in, for example, JP-A-H5-188598. Incidentally, these techniques may be used in combination.

The exposed resist film is then developed. The developer used for development is preferably an aqueous alkaline solution prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, 1,5-diazabicyclo-[4.3.0]-5-nonene), or the like in water.

The concentration of the alkaline aqueous solution is preferably 10 mass % or less. If the concentration of the aqueous alkaline solution exceeds 10 mass %, the unexposed area may be dissolved in the developer. The pH of the developer is preferably 8 to 14, and more preferably 9 to 14.

An organic solvent may also be added to the developer, for example. Examples of the organic solvent include ketones such as acetone, methyl ethyl ketone, methyl i-butyl ketone, cyclopentanone, cyclohexanone, 3-methylcyclopentanone, and 2,6-dimethylcyclohexanone; alcohols such as methanol, ethanol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide. These organic solvents may be used either alone or in combination.

The content amount of the organic solvent is preferably 100 parts by volume or less based on 100 parts by volume of the alkaline aqueous solution. If the content amount of the organic solvent exceeds 100 parts by volume, the exposed area may remain undeveloped due to a decrease in developability. An appropriate amount of a surfactant or the like may also be added to the developer.

Incidentally, after development using the aqueous alkaline solution (developer), the resist film may be rinsed with water, and dried.

EXAMPLES

Hereinbelow, the present invention is concretely described by way of examples. Note that the present invention is not limited to the following examples. In the examples, electron beams (EB) were used to expose the resist film. Note that in the case of using short-wavelength radiation such as EUV or the like, the basic resist properties are resembled and it may be well-known that there is the correlation therebetween.

Incidentally, in the examples and comparative example, the unit "parts" refers to "parts by mass", and the unit "%" refers to "mass %", unless otherwise specified. The property value measuring methods and the property evaluation methods employed in the examples and comparative example are described below.

Measurement of Mw, Mn, and dispersity (Mw/Mn)

The measurement of the Mw and the Mn were determined by gel permeation chromatography (GPC) using GPC columns (G2000HXL×2, G3000HXL×1, G4000HXL×1) manufactured by Tosoh Corporation (flow rate: 1.0 ml/min, column temperature: 40° C., eluant: tetrahydrofuran, standard: monodisperse polystyrene). The dispersity (Mw/Mn) was calculated from the measurement results.

$^1$H-NMR Analysis and $^{13}$C-NMR Analysis $^1$H-NMR analysis and $^{13}$C-NMR analysis were performed by using a spectrometer "JNM-EX270" (manufactured by JEOL Ltd.).

Sensitivity (L/S)

A resist pattern (line-and-space pattern (1L1S)) including a line part and a space part (trench) defined by the adjacent line parts was formed by changing dose. A dose at which a line-and-space pattern including a line part having a line width of 150 nm and a space part having a line width of 150 nm was formed was defined as an optimum dose, and the optimum dose was evaluated as the sensitivity.

Figure 2:
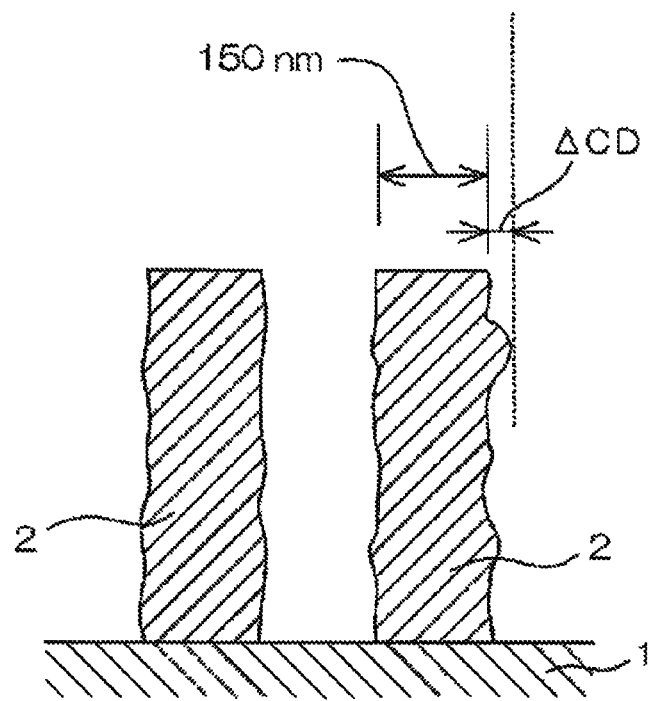
FIG. 2 is a cross-sectional view taken along the line A-A' in FIG. 1.

FIG. 1 is a plan view schematically showing a line-and-space pattern in the case of observing from above. FIG. 2 is a cross-sectional view taken along the line A-A' in FIG. 1. Note that asperities are exaggerated in FIGS. 1 and 2.

Nano Edge Roughness

A line-and-space pattern (1L1S) (design line width: 150 nm) was formed, and the line part of the line-and-space pattern was observed using a semiconductor scanning electron microscope (high-resolution FEB length measuring machine "S-9220" manufactured by Hitachi, Ltd.) to measure the height of the highest convex part that outstands from the side face of the line part. In particular, as shown in FIGS. 1 and 2, the difference ("ΔCD" in FIGS. 1 and 2) between the design line width (150 nm) and the line width ("X" in FIG. 1) in an part where the highest convex part was formed on a side face 2*a* of a line part 2 of a resist film formed on a silicon wafer 1 was measured using a CD-SEM ("S-9220" manufactured by Hitachi High-Technologies Corporation). The measured value was evaluated as nano edge roughness.

Resolution (L/S)

In the case that a line-and-space pattern (1L1S) (design line width: 50 to 150 nm) was formed while reducing the design line width by 10 nm, the minimum line width (nm) that could be formed was evaluated as the resolution.

Synthesis Example 1

Production of Resin (C-1)

53 g of p-acetoxystyrene, 48 g of the compound shown by the following formula (M-1) (hereinafter referred to as "compound (M-1)"), 7 g of azobisisobutyronitrile (hereinafter referred to as "AIBN"), and 1 g of t-dodecylmercaptan were dissolved in 150 g of propylene glycol monomethyl ether. The monomers were polymerized at 70° C. for 16 hours under a nitrogen atmosphere. After polymerization, the reaction mixture was added dropwise into 1000 g of n-hexane to coagulate and purify the copolymer. Then, after the addition of 150 g of propylene glycol monomethyl ether to the copolymer, 150 g of methanol, 37 g of triethylamine, and 7 g of water were added to the mixture. The mixture was hydrolyzed at the boiling point for 8 hours under reflux. After the reaction, the solvent and triethylamine were evaporated under reduced pressure. After dissolving the resulting copolymer in 150 g of acetone, the solution was added dropwise into 2000 g of water to coagulate the copolymer. A white powder thus produced was filtered, and dried at 50° C. overnight under reduced pressure.

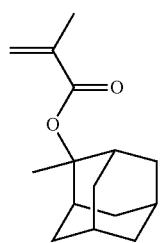

(M-1)

The resulting copolymer had an Mw of 6,000 and a dispersity (Mw/Mn) of 1.9. As a result of $^{13}$C-NMR analysis, it was found that the molar ratio of repeating units derived from p-hydroxystyrene to repeating units derived from the compound (M-1) in the copolymer was 60:40. The copolymer is hereinafter referred to as "resin (C-1)".

Example 1

10.0 g of a compound (a1-1) shown by the following formula (a1-1), 12.4 g of a compound (a2-1) shown by the following formula (a2-1), 8.8 g of triethylamine, and 2.1 g of 4-dimethylaminopyridine were dissolved in 100 g of dichloromethane. The mixture was reacted at room temperature for 24 hours with stirring. After completion of the reaction, 200 g of dichloromethane was added into the mixture. The mixture was washed twice with 100 g of a 3 mass % NaHCO$_3$ aqueous solution, washed twice with 100 g of a 3 mass % oxalic acid aqueous solution, and washed five times with 100 g of water, and the organic layer was evaporated under reduced pressure. The resulting viscous liquid was poured into 500 g of water to obtain a light yellow solid.

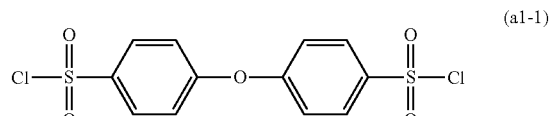

(a1-1)

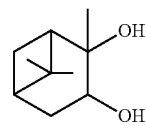

(a2-1)

The structure of the resulting compound was determined by $^1$H-NMR analysis. The results are shown below.

$^1$H-NMR (270 MHz, DMSO-d$_6$, internal standard: TMS): δ (ppm)=0.71-1.32 (18.0H), 1.40-1.60 (2.0H), 1.60-1.96 (6.0H), 1.97-2.34 (4.0H), 4.40-4.69 (4.0H), 7.10-7.25 (4.0H), 7.92-8.10 (4.0H).

From the $^1$H-NMR results, it is confirmed that the structure of the obtained compound is shown by the following formula (A-1). The compound is hereinafter referred to as "acid proliferation agent (A-1)".

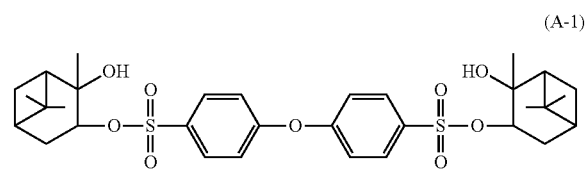 [SMILES: CC1(C)C2CC(OS(=O)(=O)c3ccc(Oc4ccc(S(=O)(=O)OC5CC6CC(C6(C)C)C5(C)O)cc4)cc3)C(C)(O)C1C2]

(A-1)

Then, 100 parts of the resin (C-1) as a resin (C), 15 parts of an acid-generating agent (D-1) as an acid-generating agent (D), 10 parts of the acid proliferation agent (A-1) as an acid proliferation agent (A), 2 parts of tri-n-octylamine as an acid diffusion controller (E), 1100 parts of ethyl lactate and 2500 parts of propylene glycol monomethyl ether acetate as a solvent (B) were mixed to obtain a mixture. The mixture was filtered through a membrane filter having pore size of 200 nm to prepare a composition solution (radiation-sensitive resin composition).

After the composition solution was applied to a silicon wafer using a "CLEAN TRACK ACT8" manufactured by Tokyo Electron, Ltd., pre-baked (PB) at 110° C. for 60 seconds (condition shown at Table 2) was subjected to form a resist film having a thickness of 50 nm. The resist film was then exposed to electron beams using a simplified electron beam exposure system ("HL800D" manufactured by Hitachi, Ltd., output: 50 KeV, current density: 5.0 A/cm$^2$). After application of electron beam, the resist film was subjected to PEB at 110° C. for 60 seconds (condition shown at Table 2). After that, the resist film was developed at 23° C. for 1 minute by a puddle method using a 2.38% tetramethylammonium hydroxide aqueous solution, rinsed with purified water, and then dried to obtain a resist having a given resist pattern. The resist thus obtained was evaluated as described above.

The resist had a sensitivity of 33 µC/cm², a nano edge roughness of 11 nm, and a resolution of 70 nm. The results are shown in Table 2.

Examples 2 and 3 and Comparative Example 1

Composition solutions (radiation-sensitive resin composition) of Examples 2 and 3 and Comparative Example 1 were prepared in the same manner as in Example 1, except for using the compounds shown in Table 1 in the amounts shown in Table 1. Resists having a given resist patterns were formed in the same manner as in Example 1 using the resulting composition solutions. The resists thus obtained were evaluated as described above. The evaluation results are shown in Table 2.

Example 4

9.6 g of a compound (a1-2) shown by the following formula (a1-2), 12.4 g of the compound (a2-1) shown by the formula (a2-1), 8.8 g of triethylamine, and 2.1 g of 4-dimethylaminopyridine were dissolved in 100 g of dichloromethane. The mixture was reacted at room temperature for 24 hours with stirring. After completion of the reaction, 200 g of dichloromethane was added into the mixture. The mixture was washed twice with 100 g of a 3 mass % NaHCO₃ aqueous solution, washed twice with 100 g of a 3 mass % oxalic acid aqueous solution, and washed five times with 100 g of water, and the organic layer was evaporated under reduced pressure. The resulting viscous liquid was poured into 500 g of water to obtain the compound shown by the following formula (A-2) (light yellow solid (A-2)). A radiation-sensitive resin composition was prepared in the same manner as in Example 1, except for using the thus obtained compound shown by the formula (A-2) in the amounts shown in Table 1. A resist having a given resist pattern was formed in the same manner as in Example 1 using the resulting composition solution. The resist thus obtained was evaluated as described above. The evaluation results are shown in Table 2.

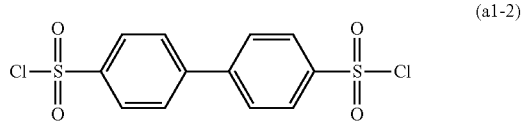

(a1-2)

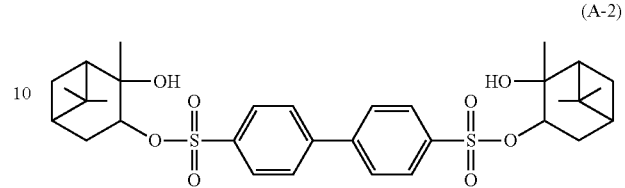

(A-2)

Example 5

10.0 g of a compound (a1-3) shown by the following formula (a1-3), 12.4 g of the compound (a2-1) shown by the formula (a2-1), 8.8 g of triethylamine, and 2.1 g of 4-dimethylaminopyridine were dissolved in 100 g of dichloromethane. The mixture was reacted at room temperature for 24 hours with stirring. After completion of the reaction, 200 g of dichloromethane was added into the mixture. The mixture was washed twice with 100 g of a 3 mass % NaHCO₃ aqueous solution, washed twice with 100 g of a 3 mass % oxalic acid aqueous solution, and washed five times with 100 g of water, and the organic layer was evaporated under reduced pressure. The resulting viscous liquid was poured into 500 g of water to obtain the compound shown by the following formula (A-3) (light yellow solid (A-3)). A radiation-sensitive resin composition was prepared in the same manner as in Example 1, except for using the compound shown by the formula (A-3) in the amounts shown in Table 1. A resist having a given resist pattern was formed in the same manner as in Example 1 using the resulting composition solution. The resist thus obtained was evaluated as described above. The evaluation results are shown in Table 2.

TABLE 1

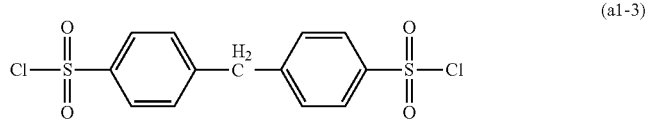

(a1-3)

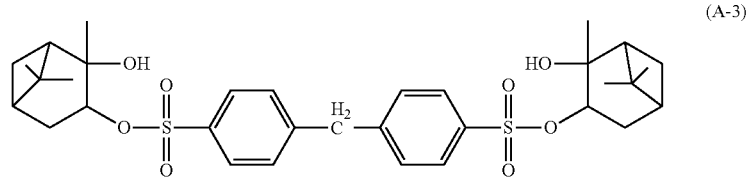

(A-3)

| | Resin (C) | | Acid-generating Agent (D) | | Acid proliferation agent (A) | | Acid diffusion controller (E) | | Solvent (B) | |
|---|---|---|---|---|---|---|---|---|---|---|
| | Type | Amount (parts) | Type | Amount (parts) | Type | Amount (parts) | Type | Amount (parts) | Type | Amount (parts) |
| Example 1 | C-1 | 100 | D-1 | 15 | A-1 | 10 | E-1 | 2 | B-1 | 1100 |
| | | | | | | | | | B-2 | 2500 |
| Example 2 | C-1 | 100 | D-2 | 15 | A-1 | 10 | E-1 | 2 | B-1 | 1100 |
| | | | | | | | | | B-2 | 2500 |
| Example 3 | C-1 | 100 | D-3 | 15 | A-1 | 10 | E-1 | 2 | B-1 | 1100 |
| | | | | | | | | | B-2 | 2500 |
| Example 4 | C-1 | 100 | D-1 | 15 | A-2 | 10 | E-1 | 2 | B-1 | 1100 |
| | | | | | | | | | B-2 | 2500 |

TABLE 1-continued

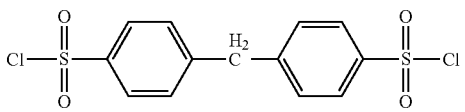 [SMILES: O=S(=O)(Cl)c1ccc(Cc2ccc(S(=O)(=O)Cl)cc2)cc1]

| | Resin (C) | | Acid-generating Agent (D) | | Acid proliferation agent (A) | | Acid diffusion controller (E) | | Solvent (B) | |
|---|---|---|---|---|---|---|---|---|---|---|
| | Type | Amount (parts) | Type | Amount (parts) | Type | Amount (parts) | Type | Amount (parts) | Type | Amount (parts) |
| Example 5 | C-1 | 100 | D-1 | 15 | A-3 | 10 | E-1 | 2 | B-1 | 1100 |
| | | | | | | | | | B-2 | 2500 |
| Comparative Example 1 | C-1 | 100 | D-1 | 15 | — | — | E-1 | 2 | B-1 | 1100 |
| | | | | | | | | | B-2 | 2500 |

TABLE 2

| | PB conditions | | PEB conditions | | Sensitivity | Nano edge roughness | Resolution |
|---|---|---|---|---|---|---|---|
| | Temp. (° C.) | Time (sec) | Temp. (° C.) | Time (sec) | (μC/cm²) | (nm) | (nm) |
| Example 1 | 110 | 60 | 110 | 60 | 33 | 11 | 70 |
| Example 2 | 110 | 60 | 110 | 60 | 35 | 11 | 80 |
| Example 3 | 110 | 60 | 110 | 60 | 30 | 11 | 70 |
| Example 4 | 110 | 60 | 110 | 60 | 35 | 12 | 70 |
| Example 5 | 110 | 60 | 110 | 60 | 37 | 12 | 70 |
| Comparative Example 1 | 110 | 60 | 110 | 60 | 42 | 13 | 80 |

The details of each component used in the examples and comparative example are shown below.

Acid-Generating Agent (D)

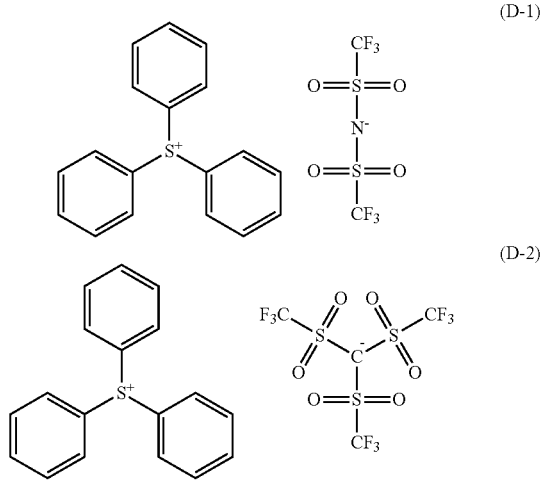

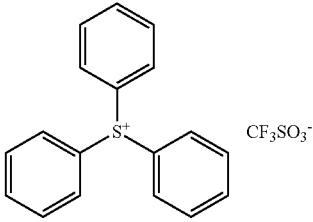

Acid diffusion controller (E-1): tri-n-octylamine
Solvent (B-1): ethyl lactate
Solvent (B-2): propylene glycol monomethyl ether acetate As is clear from the results shown in Table 2, it was confirmed that the radiation-sensitive resin compositions of Examples 1 to 5 could form a resist exhibiting excellent sensitivity, being superior in nano edge roughness, and exhibiting excellent resolution, as compared with the radiation-sensitive resin composition of Comparative Example 1.

The radiation-sensitive resin composition according to the embodiment of the present invention may suitably be used as a material for forming a resist film that is used for microfabrication employed in a lithographic process that utilizes EB, EUV, or X-rays (particularly production of semiconductor devices), and may be very useful as a material that can form a chemically-amplified resist used for production of semiconductor devices that are expected to be further miniaturized in the future.

Obviously, numerous modifications and variations of the present invention are possible in light of the above teachings. It is therefore to be understood that within the scope of the appended claims, the invention may be practiced otherwise than as specifically described herein.

The invention claimed is:
1. A radiation-sensitive resin composition comprising:
a compound;
a solvent; and
a resin comprising an acid-labile group, the compound being a compound shown by a compound shown by formula (A3), a compound shown by formula (A4), or a combination thereof,

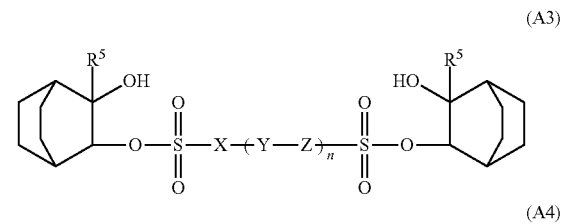

wherein
each of X and Z independently represents a substituted or unsubstituted divalent hydrocarbon group having 1 to 25 carbon atoms,
Y represents a single bond or any one of groups shown by formulas (1-1) to (1-6),

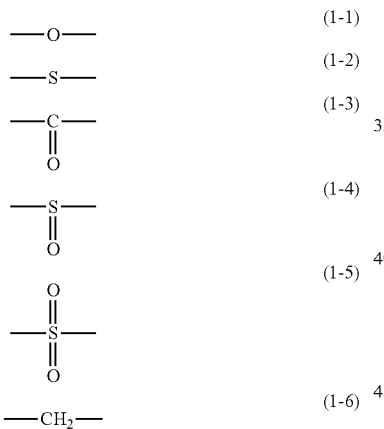

n represents an integer from 0 to 5, and
each $R^5$ independently represents a substituted or unsubstituted hydrocarbon group having 1 to 25 carbon atoms.

2. The radiation-sensitive resin composition according to claim 1, wherein each of X and Z in the formulas (A3) and (A4) independently represents a substituted or unsubstituted divalent aromatic group having 1 to 25 carbon atoms.

3. The radiation-sensitive resin composition according to claim 1, wherein Y in the formulas (A3) and (A4) represents a single bond, the group shown by the formula (1-1), or the group shown by the formula (1-6).

4. The radiation-sensitive resin composition according to claim 1, further comprising a radiation-sensitive acid-generating agent.

5. The radiation-sensitive resin composition according to claim 4, wherein a content of the radiation-sensitive acid-generating agent is 0.5 to 30 parts by mass based on 100 parts by mass of the resin.

6. The radiation-sensitive resin composition according to claim 1, further comprising an acid diffusion controller.

7. The radiation-sensitive resin composition according to claim 6, wherein the acid diffusion controller includes a photosensitive basic compound.

8. The radiation-sensitive resin composition according to claim 6, wherein a content of the acid diffusion controller is 0.005 to 20 parts by mass based on 100 parts by mass of the resin.

9. A compound shown by formula (A3) or formula (A4),

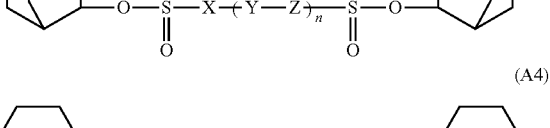

wherein
each of X and Z independently represents a substituted or unsubstituted divalent hydrocarbon group having 1 to 25 carbon atoms,
Y represents a single bond or any one of groups shown by formulas (1-1) to (1-6),

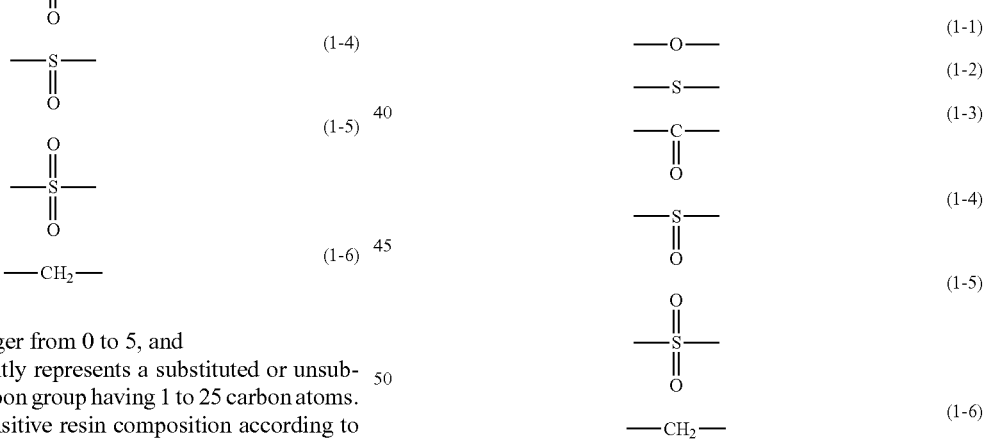

n represents an integer from 0 to 5, and
each $R^5$ independently represents a substituted or unsubstituted hydrocarbon group having 1 to 25 carbon atoms.

10. The compound according to claim 9, wherein each of X and Z in the formulas (A3) and (A4) independently represents a substituted or unsubstituted divalent aromatic group having 1 to 25 carbon atoms.

11. The compound according to claim 9, wherein Y in the formulas (A3) and (A4) represents a single bond, the group shown by the formula (1-1), or the group shown by the formula (1-6).

* * * * *